United States Patent
Humphris et al.

(10) Patent No.: US 9,304,144 B2
(45) Date of Patent: Apr. 5, 2016

(54) MULTIPLE PROBE ACTUATION

(71) Applicant: INFINITESIMA LIMITED, Abingdon (GB)

(72) Inventors: Andrew Humphris, Abingdon (GB); Andrew Neil Farley, London (GB)

(73) Assignee: INFINITESIMA LIMITED, Abingdon (GB)

( * ) Notice: Subject to any disclaimer, the term of this patent is extended or adjusted under 35 U.S.C. 154(b) by 0 days.

(21) Appl. No.: 14/434,844

(22) PCT Filed: Oct. 9, 2013

(86) PCT No.: PCT/GB2013/052633
§ 371 (c)(1),
(2) Date: Apr. 10, 2015

(87) PCT Pub. No.: WO2014/057268
PCT Pub. Date: Apr. 17, 2014

(65) Prior Publication Data
US 2015/0285836 A1 Oct. 8, 2015

(30) Foreign Application Priority Data
Oct. 12, 2012 (GB) .................................. 1218350.5

(51) Int. Cl.
*G01Q 10/00* (2010.01)
*G01Q 10/04* (2010.01)
(Continued)

(52) U.S. Cl.
CPC .............. *G01Q 10/00* (2013.01); *G01N 29/036* (2013.01); *G01N 29/2418* (2013.01);
(Continued)

(58) Field of Classification Search
USPC .................................................. 850/1, 13, 50
See application file for complete search history.

(56) References Cited

U.S. PATENT DOCUMENTS 5,144,150 A 9/1992 Yoshizumi et al.
5,929,440 A 7/1999 Fisher
(Continued)

FOREIGN PATENT DOCUMENTS

DE 3720293 A1 12/1988
EP 1577660 A1 9/2005
(Continued)

OTHER PUBLICATIONS

International Search Report mailed Nov. 15, 2013 in International Application No. PCT/GB2013/052633, filed Oct. 9, 2013.
(Continued)

*Primary Examiner* — Kiet T Nguyen
(74) *Attorney, Agent, or Firm* — Hauptman Ham, LLP

(57) ABSTRACT

A method of actuating a plurality of probes by delivering photothermal energy to the probes so that the probes are heated and deform relative to a sample. The photothermal energy is delivered to the probes by: directing an input beam into an optical device; transforming the input beam with the optical device into a plurality of actuation beamlets which are not parallel with each other; and scanning the actuation beamlets across the probes, optionally via an objective lens. A spacing between the actuation beamlets is different to a spacing between the probes so that only a subset (typically only one) of the actuation beamlets illuminates a probe at any instant. As the actuation beamlets scan across the probes the probes are illuminated in an illumination sequence. The actuation beamlets are controlled so that different amounts of photothermal energy are delivered to at least two of the probes during the illumination sequence.

19 Claims, 9 Drawing Sheets

(51) Int. Cl.
*G01Q 20/02* (2010.01)
*G01Q 70/06* (2010.01)
*G01N 29/036* (2006.01)
*G01N 29/24* (2006.01)

(52) U.S. Cl.
CPC ............ *G01Q 10/045* (2013.01); *G01Q 20/02* (2013.01); *G01Q 70/06* (2013.01); *G01N 2291/0255* (2013.01); *G01N 2291/0256* (2013.01); *G01N 2291/106* (2013.01)

(56) References Cited

U.S. PATENT DOCUMENTS

| | | |
|---|---|---|
| 6,678,056 B2 | 1/2004 | Downs |
| 6,906,450 B2 | 6/2005 | Tamayo De Miguel et al. |
| 2003/0047675 A1 | 3/2003 | Proksch et al. |
| 2006/0162455 A1 | 7/2006 | Kawakatsu |
| 2010/0139406 A1 | 6/2010 | Stievater et al. |
| 2015/0219685 A1* | 8/2015 | Humphris ............ G01Q 10/045 850/1 |

FOREIGN PATENT DOCUMENTS

| | | |
|---|---|---|
| EP | 1892727 A1 | 2/2008 |
| WO | 03/019241 A2 | 3/2003 |
| WO | 2010067129 A1 | 6/2010 |
| WO | 2012104625 A1 | 8/2012 |

OTHER PUBLICATIONS

Written Opinion mailed Nov. 15, 2013 in International Application No. PCT/GB2013/052633, filed Oct. 9, 2013.
Search Report mailed Feb. 25, 2013 in Great Britain Application No. 1218350.5.

* cited by examiner

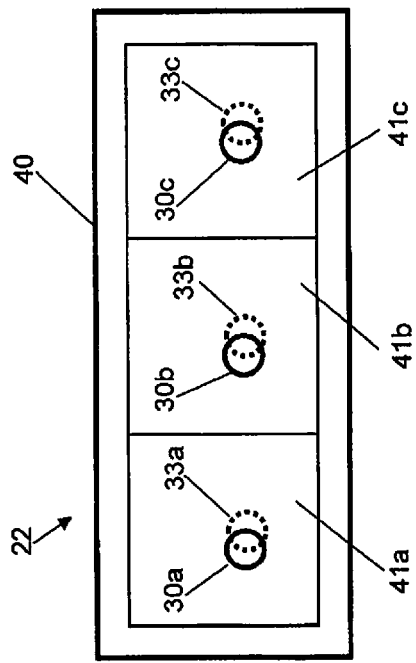
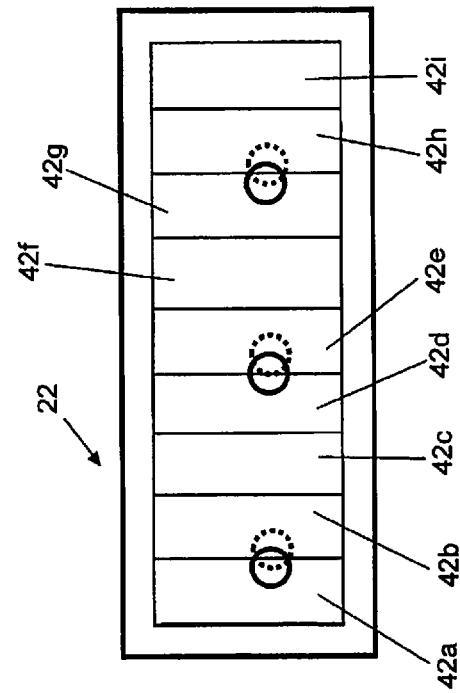
Figure 3
Figure 4

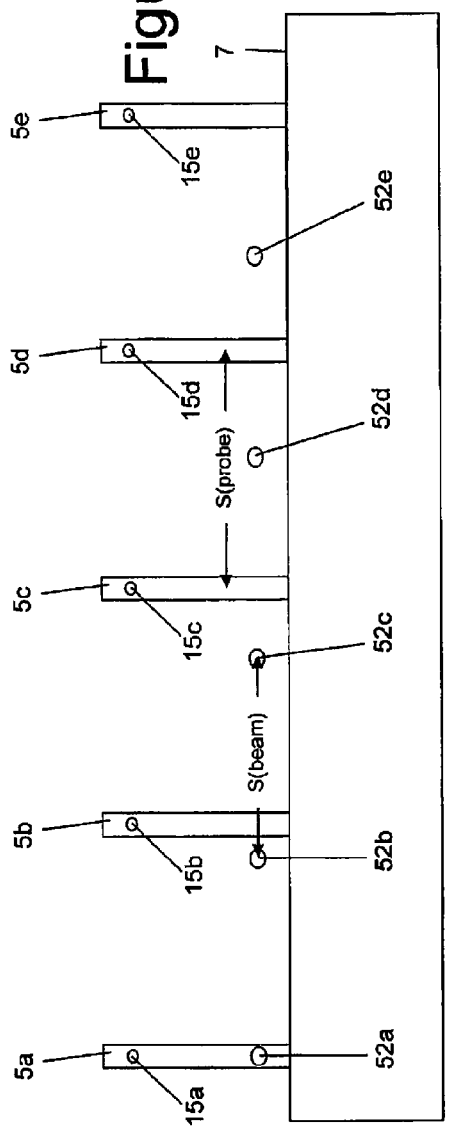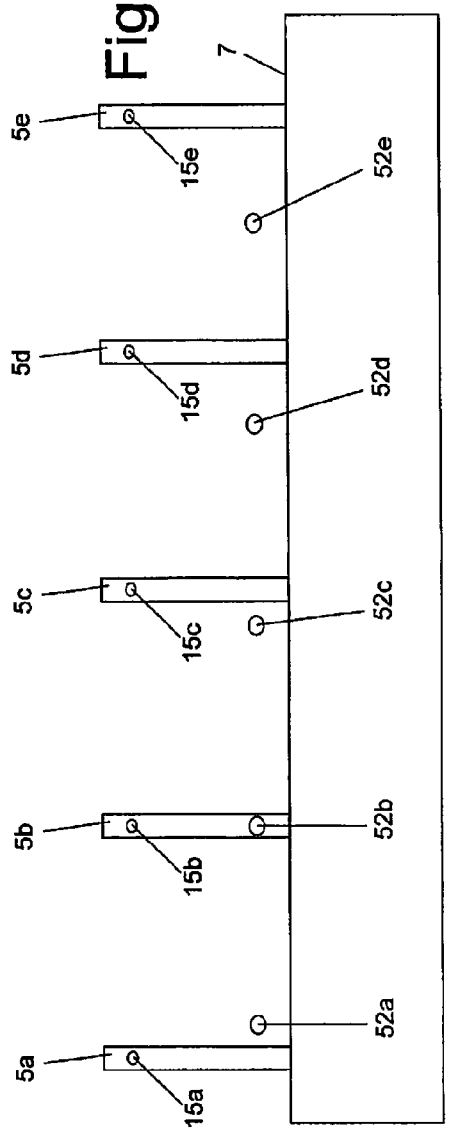

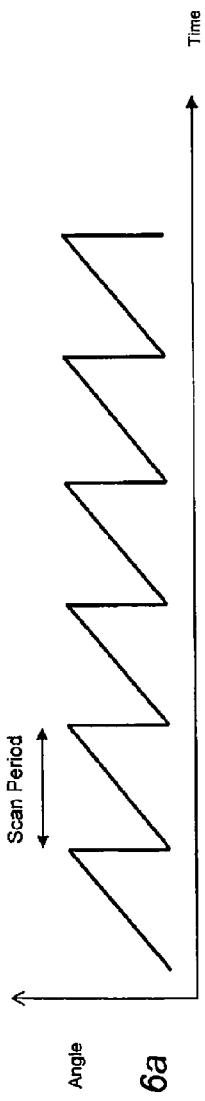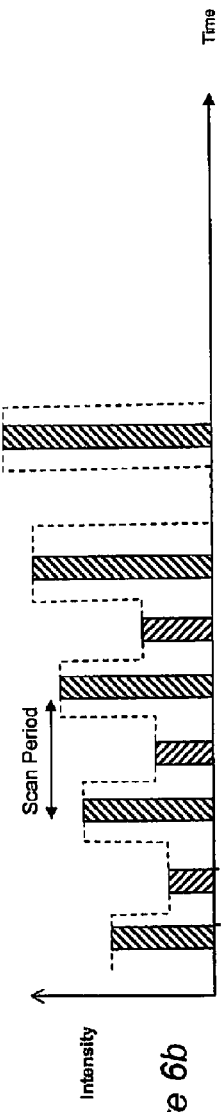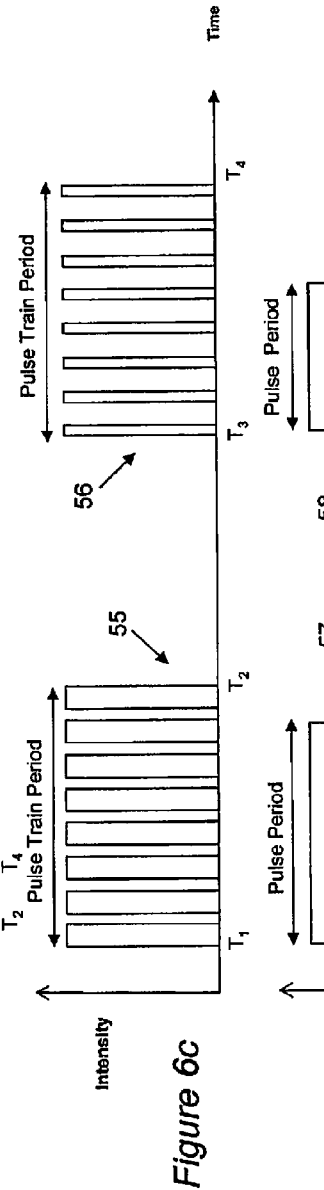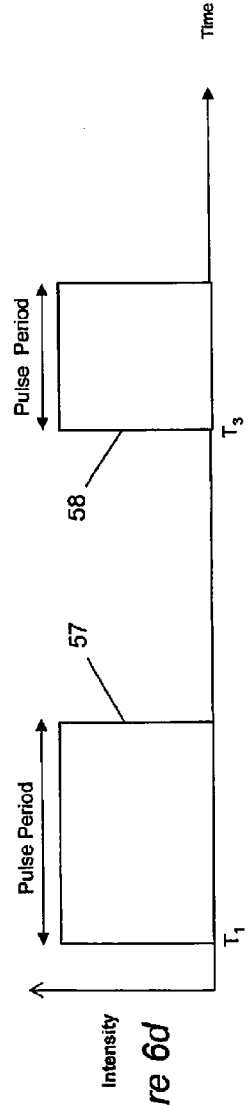

MULTIPLE PROBE ACTUATION

RELATED APPLICATIONS

The present application is a National Phase of International Application Number PCT/GB2013/052633, filed Oct. 9, 2013, and claims priority from Great Britain Application Number 1218350.5, filed Oct. 12, 2012.

FIELD OF THE INVENTION

The present invention relates to a method of actuating a plurality of probes, and apparatus operable to perform such a method.

BACKGROUND OF THE INVENTION

The speed of scanning in a probe microscope can be increased by operating two or more cantilevers in parallel, such that data is acquired simultaneously from each probe. Parallel operation in scanning probe microscopy (SPM) is a challenge because multiple probe detection must be implemented as well as independent actuation systems for each cantilever. As a result, parallel SPM systems have in the past differed significantly from conventional SPM systems. For example, some systems have deployed cantilevers with integrated piezo-resistive sensors, and integrated zinc oxide Z-actuators (Quate et al Applied Physics Letters vol 67 No 26 3918 (1995)). A major difficulty with such integrated systems is the complexity and corresponding cost of the sensors. The designs are also inflexible since changing a simple parameter such as the pitch or spring constant of the cantilevers also requires a redesign of the layout and costly fabrication. As a result, parallel SPM systems of this sort have not been widely used. There is therefore a need for a parallel probe microscope that is flexible in operation and configuration. Furthermore, such a system should incorporate a probe detection system and a probe actuation system that have at least the performance of conventional SPM, while retaining compatibility with cantilever probes widely used in SPM.

Conventional probe microscopes employ piezo-electric elements to scan the cantilever or specimen with nanometer level accuracy or better. However, such piezo-elements often have a limited speed of response due to their size and mechanical characteristics. Smaller elements which can be integrated into the cantilever can be employed for fast scanning applications but the required fabrication and electrical connection is a challenge. Photothermal actuation has therefore been developed, in which an infra-red laser is focused onto a cantilever and used to induce photothermal bending of the cantilever for both z-actuation and resonant excitation (Yamashita et al, Rev. Sci. Instrum. Vol 78, 083702 (2007). This approach is powerful and flexible, and can achieve a rapid response time due to the small size and short thermal time constant of the micromechanical cantilever. However this approach has not been used for multiple probe control due to the increased number of optical components needed for alignment and focusing.

SUMMARY OF THE INVENTION

A first aspect of the invention provides a method of actuating a plurality of probes by delivering photothermal energy to the probes so that the probes are heated and deform relative to a sample, wherein the photothermal energy is delivered to the probes by: directing an input beam into an optical device; transforming the input beam with the optical device into a plurality of actuation beamlets which are not parallel with each other; scanning the actuation beamlets across the probes (optionally via an objective lens) so that only a subset (typically only one) of the actuation beamlets illuminates a probe at any instant, and as the actuation beamlets scan across the probes the probes are illuminated in an illumination sequence; and controlling the actuation beamlets so that different amounts of photothermal energy are delivered to at least two of the probes during the illumination sequence. Typically only a subset (for instance only one) of the probes is illuminated by an actuation beamlet at any instant.

A further aspect of the invention provides apparatus arranged to perform the above method.

Instead of using multiple actuation beams, each generated by a respective laser, a single input beam is transformed into a plurality of actuation beamlets which are then directed sequentially (typically one-by-one) onto the probes. The power and/or angle of the actuation beamlets can then be controlled in order to independently modulate the positions of the probes relative to the sample.

The positions of subsets of the probes can thus be controlled independently of the other probes, for instance in order to independently control each probe's separation from the sample for imaging purposes, or to move one or more of the probes into an imaging position whilst leaving the rest of the probes in an inactive position in which they do not interact with the sample.

The invention enables the full width of a large array of probes to be scanned with only a small range of scanning motion.

Where an objective lens is provided, then typically the probes lie in a focal plane of the objective lens.

The spacing between adjacent actuation beamlets may be constant across the array of beamlets or may vary in a regular or irregular manner. Similarly the spacing between adjacent probes may be constant across the array of probes or may vary in a regular or irregular manner. In general terms a spacing between at least one adjacent pair of the actuation beamlets in a focal plane of the objective lens is typically different to a spacing between at least one adjacent pair of the probes.

In a preferred embodiment a spacing between each adjacent pair of the actuation beamlets in a focal plane of the objective lens is different to a spacing between each adjacent pair of the probes.

The spacing between the (or each) adjacent pair of actuation beamlets may be greater or less than the spacing between the (or each) adjacent pair of probes. Preferably the difference in spacing is greater than a width of the probes in the scanning direction.

Typically the actuation beamlets are repeatedly scanned across the probes (optionally via an objective lens) so the probes are illuminated in a series of illumination sequences, and the actuation beamlets are controlled so that different amounts of photothermal energy are delivered to at least two of the probes during one or more of the illumination sequences. Preferably each probe has a thermal time constant which is longer than each of the illumination sequences.

Each illumination sequence may illuminate the probes in the same order, or the order may change between sequences. All probes may be illuminated in all sequences, or some of the probes may not be illuminated in some of the sequences (for instance if they are not being used at the time). When a probe is illuminated, then it may be illuminated continuously or with a discontinuous train of illumination pulses. The actuation beamlets may remain turned on throughout the illumination sequence, or they may be turned on and off during the illumination sequence.

The actuation beamlets may be controlled directly by operation of the optical device so that different amounts of photothermal energy are delivered to at least two of the probe. However more preferably they are controlled by controlling the input beam during the illumination sequence—typically by changing its power and/or angle.

Preferably only one of the actuation beamlets illuminates a probe at any instant so the probes are illuminated one-by-one in the illumination sequence, although in other embodiments the probes may be illuminated two-by-two, three-by-three etc.

The actuation beamlets may be scanned directly by reflecting them off a scanning mirror between the optical device and the probes, or deflecting them with some other scanning device (such as an acousto-optic or electro-optic modulator) between the optical device and the probes. However more preferably the actuation beamlets are scanned indirectly by changing an angle of the input beam into the optical device, which in turn causes the actuation beamlets to scan across the probes. The angle of the input beam may be changed by a mirror, or more preferably by an acousto-optic or electro-optic modulator. Such an acousto-optic or electro-optic modulator is capable of scanning very quickly. An acousto-optic modulator typically comprises a diffractive element which diffracts the input beam, wherein the angle of the input beam is modulated over time by applying an acoustic signal to the diffractive element, the signal modulating a refractive index of the diffractive element. An electro-optic modulator typically comprises a signal-controlled element which exhibits an electro-optic effect such as the Pockels effect.

Each probe may be illuminated at the same location on the probe every time it is illuminated. Alternatively the location illuminated on a given probe may vary between scan sequences. For instance each probe may be illuminated at its base every other scan sequence (for instance the first, third and fifth sequence) and at its tip every other scan sequence (for instance the second, fourth and sixth sequence).

Each probe may comprise two or more materials with different thermal expansion coefficients which are arranged such that when the probe is heated by an actuation beam it deforms to move the probe relative to a sample. Alternatively the probes may be made of a single material—in this case they will deform due to a thermal gradient introduced by heating a region of the probe and thus inducing mechanical stress, typically between a side of the probe which is heated by the actuation beamlet and the opposite side of the probe.

The actuation beamlets can be controlled in a number of ways. Typically the probes are illuminated for a different amount of time and/or with a different power during at least one of the scan sequences.

As well as delivering different amounts of photothermal energy to different probes during a single scan sequence, different amounts of photothermal energy are typically also delivered to at least one of the probes by the actuation beam during two or more scan sequences. This enables the position of a single probe to be changed from time to time independently of the other probes.

Typically each probe has a thermal time constant associated with the deformation which is longer than each of the scan sequences.

Typically the plurality of probes comprises ten or more probes. Optionally the plurality of probes may comprise one hundred or more probes.

The probes may be arranged in a single straight line, or in a two-dimensional array.

The probes may be used in a number of applications, including (but not limited to): scanning probe microscopy, for example for extreme ultraviolet (EUV) mask inspection and review; biosensing to detect multiple biomarkers; nanolithography, such as dip pen nanolithography in which scanning probes deposit chemical compounds on a substrate; or data storage in which each probe has a heater allowing its temperature to be independently raised to melt a polymer substrate followed by an imprinting action by the probe producing a dent representing a binary digit.

BRIEF DESCRIPTION OF THE DRAWINGS

Embodiments of the invention will now be described with reference to the accompanying drawings, in which:

FIGS. 3 and 4 show two alternative photodiode arrays;

FIG. 5a shows a linear array of five probes and the illumination spots created by their associated sensing and actuation beamlets at a first time in a scan sequence;

FIG. 5b shows the linear array of five probes and the illumination spots created by their associated sensing and actuation beamlets at a second time in a scan sequence;

FIG. 6a shows a saw-tooth scanning pattern for the actuation beam;

FIGS. 6b-d show three different ways of modulating the power of the actuation beam to control the probes;

DETAILED DESCRIPTION OF EMBODIMENT(S)

Figure 1:
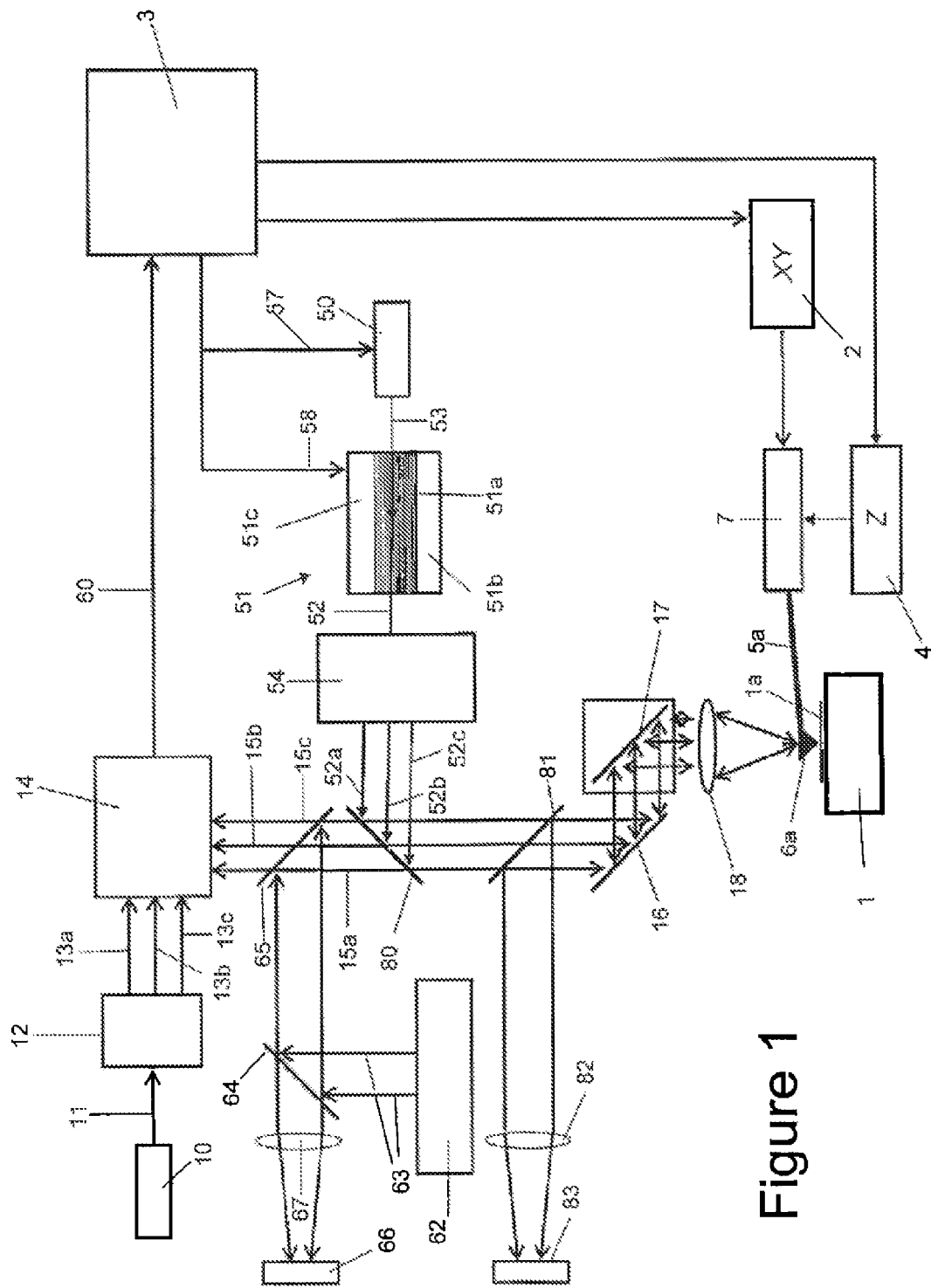
FIG. 1 is a schematic drawing of a scanning probe microscope adapted for operation with multiple probes.

With reference to FIG. 1, a scanning probe microscope that incorporates an interferometer based sensing system and photothermal actuation system in accordance with the present invention is shown. The microscope comprises a moveable stage 1 adapted to receive a sample 1a whose surface is to be investigated by an array of thermal actuated bimorph probes, only one of which is shown in FIG. 1. The scanning capability is provided by two conventional drive systems: an x,y scanner 2 operable by an SPM controller 3 to provide relative motion of the probe array in the plane (x, y) of the sample 1a; and a z positioning system comprising piezoelectric drivers 4 operable to move the probe and sample towards and away from each other (z direction) over ranges larger than that achievable by the photothermal actuation of the probe array.

The probe array comprises a linear array of cantilever beams 5a, each carrying a tip 6a which tapers to a point, and which is located towards a distal end of the cantilever beam. The other (base or proximal) end of each cantilever beam 5a is supported by a mount 7. In this embodiment, the z-positioning system 4 is connected to the probe mount 7. Alternatively, it may be connected to the sample stage 1.

The probe tip 6a comprises a three dimensional, often conical or pyramidal structure that is located at the free end of each cantilever beam 5a. The tip tapers to a point that is its closest point of interaction with a surface under interrogation. The cantilever is the beam itself, excluding the tip, that supports the tip at one end and at the other is held by the microscope apparatus. The cantilever 5a and tip 6a together are referred to as the probe.

Each probe is generally fabricated from silicon or silicon nitride. Typically, the cantilever 5a is around 50-200 µm long, 20-50 µm wide and around 0.2-2 µm thick, but this size can of course be varied according to application. The shape may also be varied: typically it is rectangular or triangular with, in the latter case, the tip in the vicinity of its apex. The tip is typically 5 µm at its base, 3-10 µm high and with an end radius of curvature of 2-20 nm. In use, the fine point at the end of the tip 6a is oriented towards the sample 1a. Recently, smaller dimension probes have been fabricated for use at faster imaging speeds. These probes have cantilevers around 5-20 µm long and 3-10 µm wide, with a correspondingly smaller tip. The tip may be formed as part of the cantilever beam fabrication process or added as a post processing step, for example, using electron beam deposition (EBD) to create a diamond like carbon (DLC) spike. Additionally, the cantilever beam is coated in a metal, typically, gold or aluminum, to increase the reflectivity of the cantilever beam when using an optical detection method.

The system is in principle capable of any conventional SPM imaging mode, and also more advanced modes developed for industrial inspection, such as, the inspection of semiconductor wafers or photo-masks. The system uses Spatial Light Modulator (SLM) units to create, steer and modulate multiple beams within the interferometer sensing system and the photothermal actuation system, thereby allowing parallel operation of an array of cantilever probes.

Figure 2:
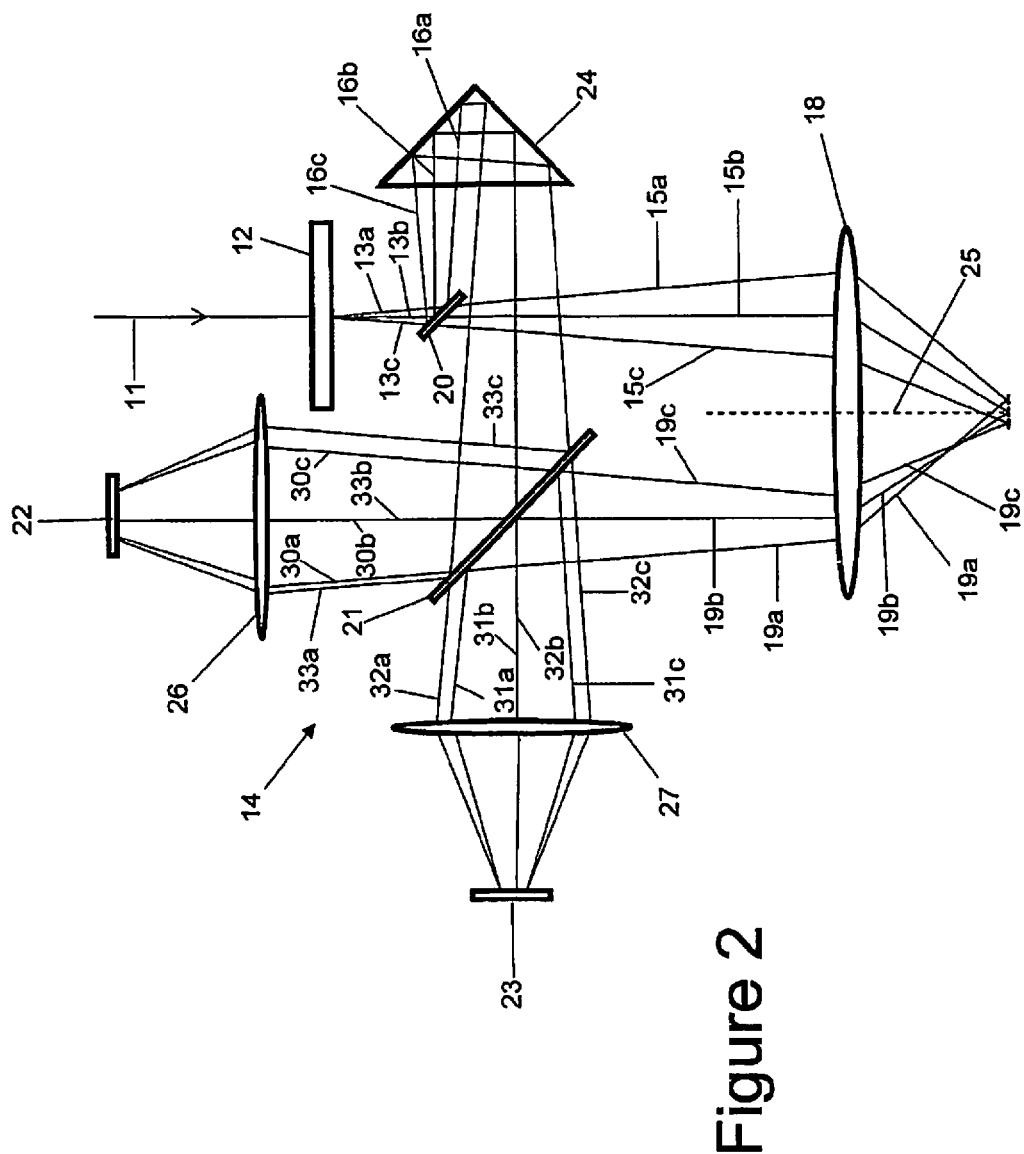
FIG. 2 illustrates the interferometer in detail.

With reference to both FIGS. 1 and 2, a detection laser 10 generates a detection input beam 11 which is incident on an SLM 12 where the beam is split into the required number of beamlets 13a-c. Typically the beam 11 is split into one beamlet 13a-c for each cantilever in the array. Alternatively the beam 11 may be split into two or more beamlets 13a-c per cantilever to measure heights or relative heights at different locations (for example one at the tip and another at the base to measure bending of the cantilever).

It would be practically difficult and complex to implement passive optical elements for this purpose, and so the SLM 12 is employed for the flexibility and ease of integration into an optical system while allowing computer control for rapid alignment. A brief description of the principles of the SLM 12 follows. Suitable SLMs are supplied by Boulder Nonlinear Systems, Colorado, USA such as their XY Series products and Hamamatsu such as their X10468 Series products.

In an exemplary SLM, in order to modulate the phase of incident light, a nematic liquid crystal SLM is aligned in a planar conformation. Here the liquid crystal director (i.e. long axis of the molecules) is oriented parallel to the polarization of the incident light. Upon application of a voltage, the molecules tilt in a direction parallel with the direction of propagation of the optical field. This causes the incident light to encounter a reduced refractive index. The change in refractive index translates directly to a change in the optical path, and consequently a phase shift for the incident light. If enough voltage is applied, the variation in refractive index ranges from the extraordinary index (for no applied voltage) to the ordinary index (maximum tilt of the molecules). A typical change in the refractive index for maximum applied voltage is 0.2. In the preferred embodiment the SLM 12 uses very large scale integration (VLSI) to address an array of liquid crystal modulators. The VLSI addressing allows for multiplexing to achieve individually addressable pixels across the entire optical aperture. This flexibility results in a randomly addressable phase mask that acts as an optical phased array with the potential for phase correction. The SLM optical head itself consists of a layer of liquid crystal sandwiched between a cover glass and a VLSI backplane.

The beamlets 13a-c then enter an interferometer 14, shown in detail in FIG. 2, where they are split by a beam splitter 20 into sensing beamlets 15a-c and reference beamlets 16a-c. The beam splitter 20 may create a lateral shift of the beam but no angular deviation.

The sensing beamlets 15a-c leave the interferometer and are reflected by a fixed mirror 16 onto a tracking mirror 17 (shown in FIG. 1 but omitted from FIG. 2) that steers the beamlets during XY scanning so that they remain optimally positioned on the cantilevers. The tracking mirror 17 comprises a scanning mirror which reflects the beamlets 15a-c at an angle which varies synchronously with the x,y scanner 2. Alternatively the tracking mirror 17 may be omitted and this steering function undertaken by the SLM 12, depending on the speed requirements. The sensing beamlets 15a-c, having been steered by the tracking mirror 17 or SLM 12, are then focused by an objective lens 18 onto the ends of the cantilevers where they are reflected back towards the objective lens 18. The lens 18 collects and collimates the reflected beamlets 19a-c and projects them back into the interferometer 14, where they are split into two components 30a-c and 31a-c by a phase shifting beamsplitter 21 and incident on photodiodes 22,23. The reference beamlets 16a-c are each split by the phase shifting beamsplitter 21 into two components 32a-c and 33a-c and incident on the photodiodes 22,23 where they are interfered with their associated reference beamlets 30a-c and 31a-c. The coating of the phase shifting beam splitter generates a phase quadrature relationship between the pair of interferogram beams produced by the overlapping reference beamlets 32a-c, 33a-c and associated reference beamlets 30a-c, 31a-c.

Although the lens 18 is illustrated as a single lens element, it will be understood that it may comprise an assembly of multiple lens elements.

After signal processing the signals are sent from the interferometer 14 to the SPM controller 3 which is adapted for parallel operation, each data channel representing the position of a point on a cantilever within the array with respect to a reference point.

The reference beamlets 16a-c are directed towards a suitably positioned retro-reflector 24, and thereafter to the beam splitter 21, where the reference beamlets are split and recombined with the two sensing beamlet components to create first and second interferograms with a relative phase shift of 90 degrees. The interferograms are detected respectively by the first and second photodiodes 22,23. Interferometric methods of extracting the path difference between two coherent beams in such a homodyne interferometer are well known in the art and so will not be described here.

The two interferograms should ideally produce signals from the photodiodes which are complementary sine and cosine signals with a phase difference of 90 degrees. The signals should have equal amplitudes with no DC offset and only depend on the displacement of the cantilever and wavelength of the laser. Due to practical limitations, such as imperfect optical components and alignment, the signals are typically not perfectly harmonic, with equal amplitude, in phase quadrature and without a DC offset. Thus known methods can be used to monitor the photodiode output signals while changing the optical path length difference in order to determine and to apply corrections for these errors.

The phase quadrature signals from the photodiodes are suitable for use with conventional interferometer reversible fringe counting and fringe subdividing techniques which, for example, may be implemented using dedicated hardware, programmable hardware such as an FPGA or as a programmed computer. Methods for subdividing or interpolating based on the arc tangent of the quadrature signals are well known and can provide sub nanometer resolution.

Note that optionally the retro-reflector 24 may be replaced by a lens and a planar mirror. This might be advantageous in a non-infinity-corrected system where the probes are not at the focal plane of the objective lens 18.

The beamlets 13*a-c* are steered by the SLM 12 so that the sensing beamlets 15*a-c* propagate at different angles relative to the optical axis 25 of the objective lens 18, such that when they reach the objective lens 18 it focuses each beamlet at the required place on the back of each cantilever in the array, in the focal plane of the lens for an infinity-corrected system. The SLM 12 achieves this diffractive beam steering with an optical phased array analogous to a radar system. Note that the angular deviations of the beamlets from the axes of the interferometer are only a few degrees at most, hence they are exaggerated in FIG. 2. The separation of the beamlets by the objective lens 18 onto the cantilever array has correspondingly been greatly exaggerated so that they can be visualized. Each beamlet is then reflected back off the cantilever and collected by the objective lens 18. The beamlet is then collimated by the objective and propagates back towards the beam splitter 21, retaining however the same magnitude of angular orientation with respect to the optic axis of the system. Meanwhile each reference beamlet has passed through the retroreflector 24 and beam splitter 21 and the matching reference beamlets are overlapped with the sensing beamlets as they propagate towards lenses 26,27 in front of multi-segment photodiodes 22 and 23. These lenses 26,27 focus the collimated beamlets down to a series of spots on the multi-segment photodiodes 22,23, each corresponding to a cantilever in the array. The position of each spot is directly related to the angular deviation of the beam from the optical axis, and hence the reference and sensing beamlets recombine to produce an intensity signal that can be related to the optical path length between them. In this way, parallel interferometric position sensing of each cantilever in the array can be achieved with sub-nanometer resolution and high bandwidth. The interferometer described herein is one example of a homodyne system. The particular system described offers a number of advantages to this application. The use of two phase quadrature interferograms enables the measurement of cantilever displacement over multiple fringes, and hence over a large displacement range. The use of a phase-shifting coating on the beamsplitter 21 used to generate the pair of phase quadrature interferograms reduces the interferometer insensitivity to polarisation effects, for example arising from changes in polarisation as the light beam is reflected from the cantilever. Examples of an interferometer based on these principles are described in U.S. Pat. No. 6,678,056 and WO2010/067129. Alternative interferometer systems capable of measuring a change in optical path length may also be employed with this invention, for example, a homodyne interferometer could be implemented using polarization methods to generate the two phase quadrature interferograms or a heterodyne implemented by using a dual frequency laser. A suitable homodyne polarisation based interferometer is described in EP 1 892 727 and a suitable heterodyne interferometer is described in U.S. Pat. No. 5,144,150 which could be adapted for use with this invention.

The position of the probe will affect the path of the reflected beamlets 19*a-c* and position of their associated spots on the photodiode 22,23. Although the angle of the probe will affect the reflected angle of the beamlet it is the height and position of the probe in the focal plane of the objective lens 18 which is particularly critical. In theory, light propagating from any angle from a single point in the focal plane of the objective lens 18 will arrive at a single point on the photodiode 22,23. This is because the focusing lens 26,27 in front of the photodiode is forming an image of the object, i.e. probe array, placed in the focal plane of the objective lens 18. One way to visualise this is to consider that light propagating from any angle from a single point in the focal plane of the objective lens 18 will produce a collimated beam of light after the objective lens which will be focused to a single point by the photodiode focusing lens 26,27. Note, this is for an infinity corrected optical system where the probe and photodiodes 22,23 are in the focal plane of the objective lens 18 and focusing lens 26,27 respectively.

Now considering a change in height of the probe, this will affect the formation of the spot on the photodiode. In fact, it will not only affect the position of the spot but also the shape of the spot, i.e. it will be out of focus. This will affect the ability to create an interferogram with the reference beam. This can be visualised by the reflected beam of light after the objective being slightly converging or diverging and thus the wave front of the beam will be distorted compared to the reference beam which will affect the contrast of the interferometer.

However it is not necessary for the sensing beamlets and reference beamlets to completely overlap on the photodiode 22,23. FIG. 3 shows part of the photodiode 22, along with the overlapping spots associated with the sensing beamlets 30*a-c* and reference beamlets 33*a-c*. The region where the beams overlap will form an interferogram and the larger the overlap the greater the intensity change of the constructive and destructive interference associated with a path length change between the sensing and reference beamlets. The regions which do not overlap simply form a DC offset on the intensity measured by the photodiode. If the degree of overlap between the spots changes, the magnitude of the intensity variation due to the interference will change, but the average DC offset measured will remain the same. Obviously it is preferred to maximise the overlap of the spots and thus signal to noise ratio, however, variations in the overlap can be accommodated.

The photodiode 22 has a body 40 and three photosensitive regions 41*a-c*. The optical system is configured such as to direct each overlapping pair of beamlets onto the centre of a respective one of the photosensitive regions 41*a-c*, so that the output of each region 41*a-c* represents the true instantaneous height of an associated one of the probes in the z direction. This is independent of the position of the base of the probe relative to the tip i.e. of the deflection.

In the case of FIG. 3 the intensity of each interferogram is monitored independently as each interferogram is located on a separate region 41*a-c* of the photodiode 22. The pitch and position of the interferograms is controlled by the magnification of the optical system which is determined by the focal length of the photodiode lens 26,27 divided by the focal length of the objective lens 18.

Optionally a greater number of photodiode regions than interferograms can be used as shown in FIG. 4 in which the photodiode 22 has nine regions 42*a-i* and the regions over which each interferogram falls can be summed to determine the interferogram's intensity. This allows for adjustments in pitch of the interferograms which may be required to accommodate changes in probe pitch.

Note that it is possible to use a 2D photodiode array if a 2D array of levers and thus interferograms is to be measured.

Returning to FIG. 1, the microscope has a photothermal sequential actuation system for bending the probes which will now be described. Light from an IR laser 50 is incident on an acoustic-optic modulator (AOM) 51 comprising a transparent crystal 51a (typically tellurium dioxide ($TeO_2$), crystalline quartz, or fused silica), a piezoelectric transducer 51b attached to the crystal 51a, and an absorber 51c. The transducer 51b is used to excite a sound wave in the crystal 51a with a frequency of the order of 100 MHz. An input beam 53 from the laser 50 then experiences Bragg diffraction at the traveling periodic refractive index grating generated by the sound wave. The deflected input beam 52 has a slightly modified optical frequency (increased or decreased by the frequency of the sound wave) and a slightly different direction. The change in direction is smaller than shown in FIG. 1, because the wave number of the sound wave is very small compared with that of the input beam 53. The frequency and direction of the deflected input beam 52 can be controlled via the frequency of the sound wave, whereas the acoustic power is the control for the optical powers. For sufficiently high acoustic power, more than 50% of the optical power can be diffracted—in extreme cases, even more than 95%. The acoustic wave is absorbed at the other end of the crystal by the absorber 51c.

Within the AOM 51 the acoustic wave is provided by a radio frequency (RF) signal 58 to the AOM, controlled by an AOM controller (not shown). This AOM controller has three components, a Voltage Controlled Oscillator (VCO); a Voltage Variable Attenuator (VVA); and an amplifier. The VCO provides a RF sine-wave output, the frequency of the RF output is determined by an applied control voltage, and varies approximately linearly with it. The VVA attenuates the output from the VCO, the degree of attenuation is controlled by varying the applied control voltage to the VVA. The amplifier amplifies the output of the VVA, such that the RF output is sufficient to drive the AOM. The response of the AOM varies with the frequency and amplitude of the input RF signal.

The deflected input beam 52 is then incident on an SLM 54 where the beam 52 is split into the required number of actuation beamlets 52a-c. Typically the beam 52 is split into one actuation beamlet 52a-c for every cantilever in the array. The SLM 54 is similar to the SLM 12 which has already been described so will not be described again. Note that in another embodiment the order of the AOM 51 and the SLM 54 may be reversed so the input beam 52 is first split into beamlets by the SLM 54, and those beamlets are then input into the AOM 51 which scans them across the probes.

The actuation beamlets 52a-c are reflected off a mirror 80 which reflects the wavelength of the beamlets 52a-c but transmits other wavelengths. The beamlets 52a-c then pass to the tracking mirror 17 (shared with the interferometer 14) which maintains them in position on the cantilevers as they are scanned in XY. The actuation beamlets 52a-c are then focused by the objective lens 18 onto the cantilevers.

FIG. 5a is a schematic view of five cantilevers 5a-e viewed from above. The cantilevers are illuminated by sensing beamlets 15a-e at their distal ends above the tip 6a (which is on the opposite side of the cantilever and hence not shown in FIG. 5). The cantilevers are positioned in the focal plane of the objective lens 18 and spaced apart equally with a centre-to-centre spacing S(probe) between them. The actuation beamlets 52a-e generate spots in the focal plane of the objective lens 18 which are also spaced apart equally but with a different centre-to-centre spacing S(beam) between them. In this case S(probe)>S(beam). Since the spacing S(beam) between the actuation beamlets is different to the spacing S(probe) between the probes only a subset of the actuation beamlets illuminates a probe at any instant. Thus in the instant shown in FIG. 5a only a single probe 5a is being illuminated.

The actuation beamlets 52a-e are scanned across the probes in a series of scan sequences by operating the AOM 51 to change the angle of the input beam 52 into the SLM 54. FIG. 5a shows a first instant in the scan sequence in which only the probe 5a is illuminated. As the beamlets 52a-c move together to the right, beamlet 52a moves off the probe 5a and beamlet 52b moves onto the probe 5b as shown in FIG. 5b, and so on. Thus as the actuation beamlets 52a-e scan across the probes, the probes are illuminated sequentially providing an effect analogous to a moiré pattern. In this illumination sequence the probes are illuminated one-by-one between adjacent probes from left to right—that is, in the sequence 5a,5b,5c,5d,5e. However other illumination sequences are possible—for instance the probes may be illuminated two-by-two, or in a sequence which does not progress regularly between adjacent probes (for instance the sequence may be random or irregular such as 5a,5e,5b,5d,5c).

In the embodiment of FIG. 5a the spacing S(probe) between each adjacent pair of probes is constant across the array of probes and the spacing S(beam) between each adjacent pair of spots is also constant across the array of beamlets. However S(beam) and/or S(probe) may vary across the array depending on the illumination sequence which is required. Also S(beam) may be constant or may vary over time from scan sequence to scan sequence. In general terms the spacing between at least one adjacent pair of the actuation beamlets in the focal plane of the objective lens is typically different to a spacing between at least one adjacent pair of the probes.

The cantilevers have a width W and are widely spaced relative to their width so S(probe) is typically more than 5 W and may be as high as 10 W. By way of example the probes may have a width W of 10 μm and a spacing S(probe) of 100 μm. In the absence of the SLM 54 (that is, if only the diffracted beam 52 from the AOM was scanned across the probes) this would require the AOM 51 to scan the beam 52 over the full 400 μm width of the probe array. This large range of scanning motion may be difficult to achieve with some AOMs or may limit the maximum speed with which the beam can be scanned. The SLM 54 enables the full width of the array of probes to be scanned but with only a small range of scanning motion required from the AOM 51—in the above example only 50 μm of scanning motion is required. The small scale, high frequency beam deflections provided by the AOM 51 will not interfere with the operation of the SLM 54.

The photothermal actuation system is capable of controlling the cantilevers in a number of ways, with great flexibility and control. For example, by steering the actuation beamlets 52a-e to the base of the cantilevers, the photothermal effect can be used to deflect the cantilever up and down for the purposes of cantilever selection, or alternatively, z-actuation in the case of conventional SPM feedback control.

With a suitable objective lens 18 it is possible to achieve a spot size for the actuation beamlets 52a-e and sensing beamlets 15a-g of only a few microns, allowing the precise application of infra-red radiation to a specific location on the cantilever as required for efficient photothermal actuation. Using the SLMs 12,54 it is also possible to control the size of the focused spot produced by each beamlet as shown in FIGS. 5 and 6 in which the actuation beamlets 52a-e create spots which are larger than those created by the sensing beamlets 15a-e.

The cantilevers 5a-e are thermal biomorph structures, the materials of which undergo differential expansion when heated. That is, they are composed of two (or more) materials, with differing thermal expansions. Typically, this will be a silicon or silicon nitride base with a gold or aluminium coating. The coating extends the length of the cantilever and covers the reverse side from the tip. The actuation light source 50 preferably emits light 53 of one or more wavelengths at which there is a maximum or peak in the absorption spectrum for the particular coating. For example the wavelength may be around the aluminium absorption peak at ~810 nm. Other coating/wavelength combinations can be used, for example gold has a higher absorption below 500 nm light. When this light is incident on the coating side of the cantilevers, the aluminium expands to a greater degree than the silicon nitride, bending the cantilever such that the tip moves downwards, towards the sample. If illumination intensity is increased, the tip therefore moves closer to the sample surface. Conversely, if the intensity is lowered, bending is decreased and the tips are moved away from the sample. Other arrangements of coating and base materials may result in bending in an opposite direction in response to illumination.

Referring to FIG. 1: the actuation light source 50 and AOM 51 are controlled by the SPM controller 3 which controls the intensity of the light 53 emitted from the actuation light source 50 and thus controls the intensity of the actuation beamlets 52a-e at a high modulation rate of typically 100's of kHz to 10's of MHz. The intensity of the beam 52 determines the degree of bend exhibited by the thermal bimorph probes (regardless of their material specifics) and so governs the tip—sample separation distance during the course of a scan.

The SLM 54 could be operated to independently modulate the intensities of the actuation beamlets 52a-c but typically SLMs are not capable of modulating the intensity at a sufficiently high rate so it is preferred to control the actuation beamlets by modulating the light 53 from the actuation source 50. The intensity of the light 53 is modulated as the scan progresses in accordance with parameters that will now be described with reference to FIGS. 6a-d.

FIGS. 6a-d show how the AOM 51 and laser 50 are operated to independently actuate each probe. The AOM 51 sequentially directs the actuation beamlets onto the probes in a series of scan sequences, six of which are illustrated in FIG. 6a. FIG. 6a shows the variation over time of the angle of the input beam 52 with respect to the optical axis of the objective lens 2. The angle increases uniformly within each scan period from a minimum angle to a maximum angle, then returns to the minimum angle for the next scan period. Each probe is illuminated by a respective actuation beamlet for a respective part of each scan period.

FIG. 6b shows how the intensity of the actuation beamlets is modulated to independently actuate only two probes. However it should be noted that the principles illustrated in FIG. 6b can be extended to any number of probes. A first one of the probes is illuminated during a first illumination period $T_1$ to $T_2$ within each scan sequence, and a second one of the probes is illuminated during a second illumination period $T_3$ to $T_4$ within each scan sequence. The power of the input beam 53 (and hence the power of the actuation beamlets 52a-e) is modulated as shown by the dashed line in FIG. 6b, and the area of the cross-hatched rectangles show the amount of photothermal energy being delivered to each probe by an actuation beamlet during a scan sequence. Note that in this example all actuation beamlets are turned on at all times as they traverse across the probes, and are also turned on as they traverse between the probes. The intensity of the actuation beamlets is modulated so that the two probes are heated by their respective actuation beamlet by different amounts during each of the scan sequences shown in FIG. 6b Also each one of the probes is heated by its respective actuation beamlet by different amounts during at least two of the scan periods. In this example each probe is heated by a gradually increasing amount during the first three scan periods, then the second probe is no longer heated so it retracts while the first probe remains being heated for two further scan periods (so the second probe continues moving towards the sample as the first probe retracts).

The scan period (shown in FIGS. 6a and 6b) is of the order of 0.5 microseconds. The illumination period for each probe (T2-T1 and T3-T4) is of the order of 0.1 microseconds. Each probe has a thermal time constant associated with the deformation which is longer than the scan period, the thermal time constant being typically of the order of 5-10 microseconds or longer depending on the dimensions and geometry of the cantilever. This ensures that each probe does not cool down to a significant extent during the time between each successive illumination period for that probe. The thermal response of the cantilever can be approximated as an exponential function where the response due to heating is:

Deflection=constant*(1−e^(−time/thermal time constant)

and the response due to cooling is:

Deflection=constant*e^(−time/thermal time constant).

The thermal time constant may vary slightly when either heating or cooling of the cantilever beam.

Suitable AOMs are the ATD-80 series AOM manufactured by IntraAction Corp (www.intraaction.com), or AOMs available from AA Opto-Electronic, see www.aaoptoelectronic. com. The IntraAction device operates at 80 MHz, but can be driven by modulating the frequency of the RF input signal to achieve beam scanning via Bragg deflection over a range of up to 40 mrad. If this angular deflection is too small then it could be increased using a suitable lens amplification unit. It is also possible to achieve 2D scanning by using two AOM devices in series.

FIG. 6c shows another way of independently controlling the amount of photothermal energy being delivered to each probe during a scan period. In this example, instead of illuminating each probe continuously between $T_1$ and $T_2$ and between $T_3$ and $T_4$ (as in FIG. 8b) the input beam 53 is turned on and off quickly so that each probe is illuminated intermittently in a series of pulses within each illumination period (or pulse train period) and the "mark-space ratio" of the pulses is varied to control the amount of energy delivered. So in this example during a single scan sequence the first probe is illuminated by a pulse train 55 of eight relatively long pulses and the second probe is illuminated by a pulse train 56 of eight pulses which each have the same power but a shorter duration than the pulses of the pulse train 55.

FIG. 6d shows yet another way of independently controlling the amount of photothermal energy being delivered to each probe during a single scan period. In this example, instead of illuminating each probe continuously between $T_1$ and $T_2$ and between $T_3$ and $T_4$, the beam is turned on and off so the first probe is illuminated by a single relatively long pulse 57 and the second probe is illuminated by a single pulse 58 which has the same power but a shorter duration than the pulse 57.

Figure 7:
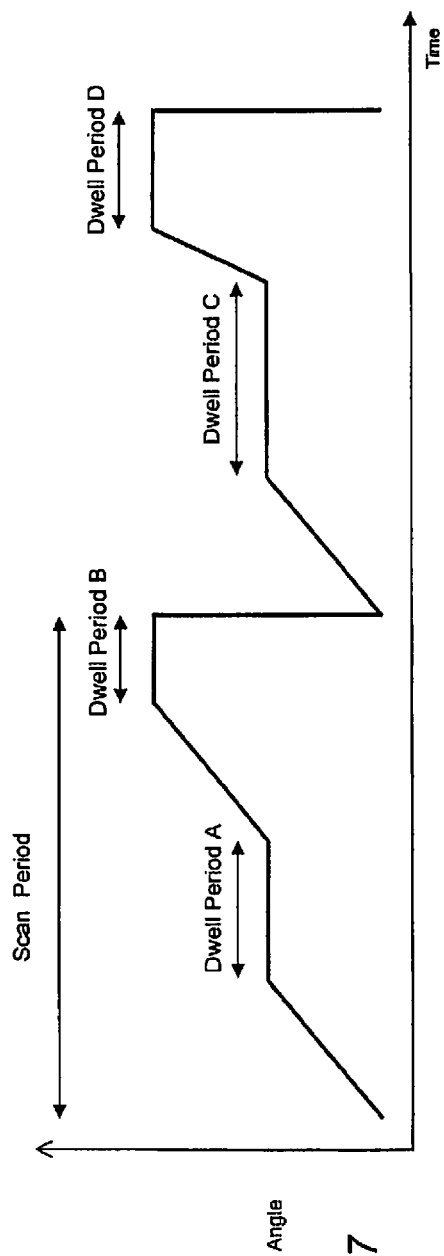
FIG. 7 shows an alternative scanning pattern which can be used to control the probes without varying the power of the input beam.

In yet a further embodiment shown in FIG. 7 the power of the input beam 53 and actuation beam 52 is kept constant and the amount of photothermal energy delivered to each probe during a single scan period is controlled instead by controlling the angle of the actuation beamlet via the AOM. FIG. 7 shows two scan sequences in which the angular sweep of the actuation beamlets is stopped as it reaches the first and second probes and held during Dwell Periods A-D. The lengths of the Dwell Periods A-D can then be controlled to independently control the amount of photothermal energy being delivered during a scan sequence. In this example Dwell Periods A-D are all different.

Precise timing of the pulses 55-58 in relation to the actuation beam position is achieved by calibration. Such calibration is desirable because:

a. the photothermal energy input to a given cantilever is controlled by timing the modulation of the actuation beamlets 52a-e with respect to the position of the actuation spot as it scans over the array. However the exact position of the actuation beam spot is unknown as it is a function of the dynamic response of the AOM 51 and the detailed optical configuration; and b. the actual motion of the probe in response to the photothermal energy input will be filtered by the thermal time constant of the probe itself.

Calibration can be achieved by using the probes themselves and the interferometer based sensing system 10,12,14. A typical calibration procedure might be as follows.

The AOM 51 is initially driven at low frequency with a sawtooth waveform of the required amplitude. This sawtooth periodically deflects the actuation beamlets 52a-e across the probes and, in the absence of laser modulation, the probes are addressed at the sawtooth frequency. The probes respond to the photothermal energy input by deflecting and then returning to zero deflection as the probe cools down, with some oscillation around zero due to the high quality factor. This initial procedure gives a rough indication of the photothermal response, the thermal time constant, and the quality factor of each probe. Further adjustments can be made by moving the central position of the sawtooth scan pattern back and forth and observing the motion of the outer cantilevers as the sawtooth scan moves off them. In this way the beamlet scan can be approximately centralised.

The frequency of the sawtooth waveform is now increased and the motion of the probes observed by the interferometer based sensing system. Any change in the scan amplitude or scan centre can be adjusted by following the above procedure. The motion of the probes will transition from the classic impulse response of a harmonic oscillator to a DC deflection with the scan modulation superposed upon it. As the scan frequency continues to increase up to the operating frequency, the address rate of the actuation beamlets exceeds the thermal relaxation time of the probes and the probes stabilise at a steady DC deflection. Some variation in deflection between probes may be apparent at this stage and can be used to calibrate their individual response functions, by increasing the energy of the input beam 53 and noting the increase in deflection of each probe. However, because the position and corresponding dwell time of the IR laser is not a priori known, such a calibration may be subject to a degree of error.

It is now necessary to implement individual control of the probes. The AOM drive signal 58 provides an indication of the position of the actuation beamlets at any point in time, which can be obtained by relating the timing of the sawtooth waveform to the previous calibration results. However a more direction measurement could be made by inserting a 45 degree semi-reflecting mirror 81 into the beam path above the objective lens to create a weak reference beam. The reference beam then passes through an equivalent lens 82 and is focused onto a photodiode 83 (or equivalent) that effectively parallels the operation of the probe array but with a much faster response. The signal from the photodiode 83 can be used for timing purposes and may be more accurate than the AOM drive signal 58. Alignment and calibration of the photodiode 83 can be undertaken at lower frequencies, alongside the probe array, as above.

Sequential scanning actuation can be implemented using a variety of timing schemes but for this example the actuation scheme of FIG. 6c will be referred to. In this scheme it is necessary to trigger a pulse train 55, 56 of the required energy when the actuation beam is passing over each probe. A timing signal can be obtained by using the signal from the IR photodiode 83, which will send out a pulse train as the actuation beam passes over the probe array or alternatively by using the AOM signal once calibrated by the IR photodiode. The timing signal is then used to trigger the actuation pulse train 55, 56 for each probe. Any probe can be individually calibrated for a range of pulse train energies. Fine tuning of the position of the pulse train 55, 56 over each probe can be achieved by varying the timing of the pulse train so that it strays over one or the other side of the probe, which will be apparent from the reduction in the deflection of the probe as the IR energy is lost. In this way the pulse can be centred on the probe to ensure an accurate and reproducible photothermal actuation.

The actuation light source 50 and AOM 51 can be considered to provide the drive mechanism for both the z position feedback and the probe oscillation. That is, they are set to drive oscillation of each cantilever probe and to adjust each probe—sample separation distance during the course of a scan. Specific embodiments of the imaging modes of the SPM will now be described in more detail.

The probe microscope is especially suitable for examining large, substantially flat, surface areas to detect features on the nanometer scale, at the high speeds required for effective industrial application. A prime example of such an application is the inspection of Extreme Ultra-Violet (EUV) masks. A critical issue to be addressed for commercialization of EUV lithography is the detection and reduction of defects on the masks and in particular on blank mask. Typical defects on blank masks are either pits or particles which can originate either on the substrate, during multilayer deposition or on top of the multilayer stack. The buried defects are especially problematic, and 10 nm defects and small may be considered an issue. For example, the phase shift caused by a 3 nm variation in mask substrate flatness is sufficient to produce a printable defect. SPM is in principle well suited to the detection of such defects, but single probe instruments are too slow for industrial applications. A probe instrument of typically ten probes or more is required to achieve acceptable scan speeds. The exemplary operating mode of such an instrument, which is based on a cyclic oscillation of each probe, is described in the following section.

It may be desirable to only have a subset of the probes at an imaging position at a set height above the surface. For example with an array of ten probes it may be desirable to only have five probes (for example every other probe) at an imaging position at any one time. Then if one of the five probes becomes damaged, the five probes can be retracted from the sample 1a and the other five probes moved into position. Such slow gross probe z positioning can be achieved by the laser 50 which can operate to select or retract individual probes (or groups of probes) from the imaging position independently of the other probes in the array.

Each probe is continually monitored throughout its oscillation by the parallel interferometric detection system 14, which outputs a signal 60 for each probe that corresponds to the instantaneous position of the probe at a given point in time. Considerable amounts of data are generated in this way for a high speed scanning system. The SPM controller 3 therefore incorporates a field programmable gate array (FPGA) which is configured in order to provide the necessary processing capability. As is known in the art, alternative signal processing techniques such as digital signal processing (DSP) or a dedicated analogue or digital electronic method may be used. The probe cyclic motion typically has a frequency range of 10's of kHz to a few Mhz and sampling frequency for data recording is in the region of 100 MHz. Consequently, each cycle of probe movement is sampled in the region of 1000 to 10,000 times, which is more than sufficient to analyse the height detector signal 60 to obtain a surface height detection point for each tip in the array. There are a number of ways that the instantaneous height detection signal can be processed to derive a surface height reading for any given probe. However in the simplest case readings can be based on the lowest recorded point in the probe oscillation cycle, when the probe tip is considered to be substantially in contact (or close to contact) with the surface.

The xy scanner 2 translates the cantilever array across the surface of the sample in order to generate an image of the surface. The controller 3 ensures that the tracking mirror 17 is matched with the scan pattern driven by the scanner 2 such that light from both the IR actuation source 50 and the detection source 10 maintain their position on each probe (shown in FIG. 5) in the array as it moves. The controller 3 may calculate different drive signals for the scanner 2 and tracking mirror 17 depending on their particular construction and mechanical behaviour. If the sample is scanned the tracking mirror 17 may not be required if the sample is moved such that the probe, detection and actuation system remain in a fixed registration. Optionally the xy scanning motion is split between the probes and the sample—that is, the probes move in x and the sample is moved in y to generate the scanning motion to inspect the sample. This enables the scan to consist of long swathes across the sample. It is also possible to rotate the sample to generate an r,θ scanning arrangement.

In this way the probe array is scanned over the surface, with the microscope collecting data from each probe within the array to provide a spatial map of the surface, formed of data points with sub-nanometer vertical and horizontal resolution. It will be appreciated that many scan operating patterns can be followed to collect data, depending on the kind of inspection information required. In the case of investigating defects on EUV masks, a large surface area must be inspected due to the low levels of defects. Typically the scan pattern will follow a raster pattern, with ten probes providing a data acquisition rate increase of about ten times compared with the case of a single probe microscope.

It will be appreciated that as the array is translated in the XY plane, each probe tip will encounter a different surface segment at the low point of each probe oscillation cycle as it engages with the surface. As the surface is not completely smooth, the tip will therefore engage at different points in the oscillation cycle and the surface height of a given segment extracted as described above. No adjustments are made to the cantilever base height on a segment by segment basis, as in conventional SPM where a feedback loop operates. However for substantially flat samples scanning the array at a constant separation with the sample and not making any adjustments may be acceptable, and confer significant advantages. For example, it should be emphasized that the scan speed of the parallel probe microscope is not limited by the z-actuation feedback loop when operated in this mode, as is the case with a conventional SPM. The parallel probe microscope is capable of operating at scanning speeds considerably in excess of the limit imposed by feedback on reasonably flat samples. The height information extracted by the parallel interferometer detection system 14 represents the true instantaneous height of the probe, rather than the output of a Z actuator servo control loop as utilized in conventional SPM. However, the SPM controller 3 is used to maintain the probe array within a suitable range of the surface over longer time periods. This is achieved by processing the height data for each probe to extract a parameter that is indicative, for example, of the dwell time of the probe tip on the surface. Other parameters could be employed. These parameter values for each probe are then processed and used to drive a relatively slow z actuation control loop which adjusts the laser 50, the sole purpose of which is to maintain probe motion within set limits.

Figure 8A:
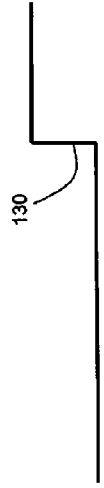
FIGS. 8a-d show an example of how the deformation of two of the probes can be controlled as they traverse steps on the sample surface.
Figure 8B:
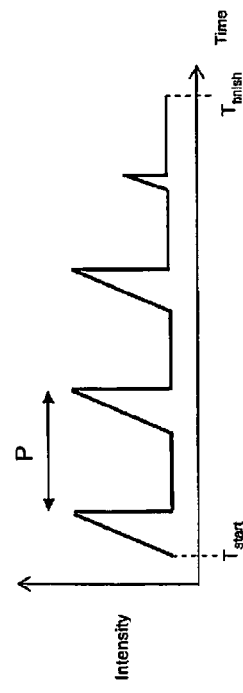
Figure 8C:
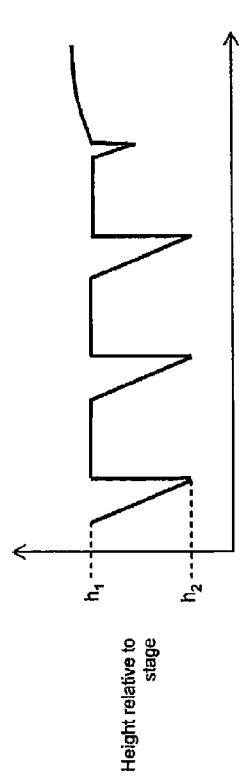

One mode of operation of the microscope of FIG. 1 is shown in FIGS. 8a-d. A first probe traverses a part of the sample with a step 130 shown in FIG. 8a. FIG. 8b shows the photothermal intensity being delivered to the first probe with respect to time over four cycles (each cycle having the same approach/retract period P). FIG. 8c shows the output of the interferometer for that probe—i.e. the height of the probe tip relative to the stage 1. The interferometer analyses the height signal of FIG. 8c to provide an indication of the point in the cycle at which the probe tip can be considered to have made contact with the sample or be proximate the sample.

During each cycle the probe starts retracted from the sample at height $h_1$, then the photothermal intensity shown in FIG. 8b is increased so the probe approaches the sample until it reaches a surface position at height $h_2$ at which the probe interacts with the sample. In response to detection of the interaction with the sample the controller 3 reduces the photothermal intensity which causes the probe to retract from the sample. After the probe has traversed the step, it can be seen that the probe is retracted at an earlier point in the cycle.

Figure 8D:
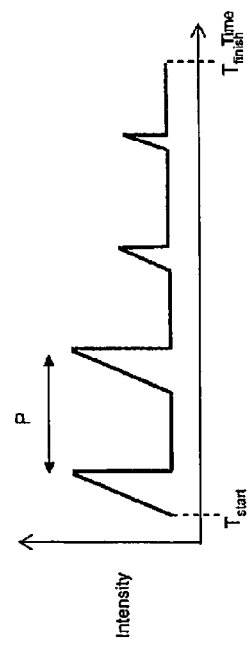

At the same time as the first probe traverses the step 130 shown in FIG. 8a, a second probe scans across another part of the sample and meets a different step. FIG. 8d shows the photothermal intensity being delivered to the second probe with respect to time over the same time period $T_{start}$ to $T_{finish}$. Note that the second probe meets a step earlier than the first probe.

The microscope uses the height signal of FIG. 8c to form an image of the sample. The height signal may be used in a number of ways to form the image. For example the image of the sample may comprise a plurality of pixels, each pixel varying in accordance with the value of the height signal when the surface position is detected for a given single cycle of the motion of the probe towards and away from the sample. Alternatively each pixel of the image may be derived from plural height data samples collected from the height signal over an extended portion of the probe motion during a single cycle of its motion, rather than from a single data sample for each cycle. For example plural height data samples may be collected for an extended portion of the probe motion before and/or after the surface position is detected, and these samples analysed to determine the value of a material property (such as elasticity) and that material property used as a pixel of the image. In this way an image or map of the material property across the sample can be formed.

Further details of the imaging mode described above can be found in WO2012/104625, the contents of which are incorporated herein be reference.

Optionally the microscope of FIG. 1 also has an optical system for generating an image of the beamlets on the probes, which will now be described. An illumination source 62 generates an illumination beam 63 which illuminates the probes via beam splitters 64, 65 (such as dichroic mirrors) and the objective lens 18. The beamsplitter 65 transmits the beamlets 15a-c but reflects the illumination beam 63 which has different wavelengths to the beamlets 15a-c.

Reflected or scattered light from the probes is directed onto a charge coupled device (CCD) camera 66 by a tube lens 67. The CCD camera 66 generates an image of the complete array of probes (similar to FIGS. 4a and 5b) which is input to the controller 3. The image can then be used by the controller 3 to adjust the XY position of the array of probes and/or the angles of the beamlets from the SLMs 12,54 so that the beamlets are centred on the probes prior to imaging. Once the beamlets have been crudely centred on the probes using the image from the CCD camera 66, the controller 3 can then use the signals from the interferometer photodiode 22 to adjust the XY position of the array of probes and/or the angles of the beamlets from the SLMs 12,54 so that the beamlets are accurately centred on the probes. This is done by moving the beamlet or the probe to the left side of the probe until the beamlet falls off the left edge of the probe (and the associated signal from the photodiode changes abruptly or drops below a pre-set level); then moving the beamlet or the probe to the right side of the probe until the beamlet falls off the right edge of the probe (and the associated signal from the photodiode changes abruptly or drops below a pre-set level). The beamlets or probe can then be moved to the midpoint between these points. A similar process can be used to accurately position the beamlets relative to the distal end of the cantilever.

This accurate xy alignment can be achieved by moving the probes in unison by moving the probe support 7, or more preferably by independently adjusting the angles of the beamlets from the SLMs 12,54.

Figure 9:
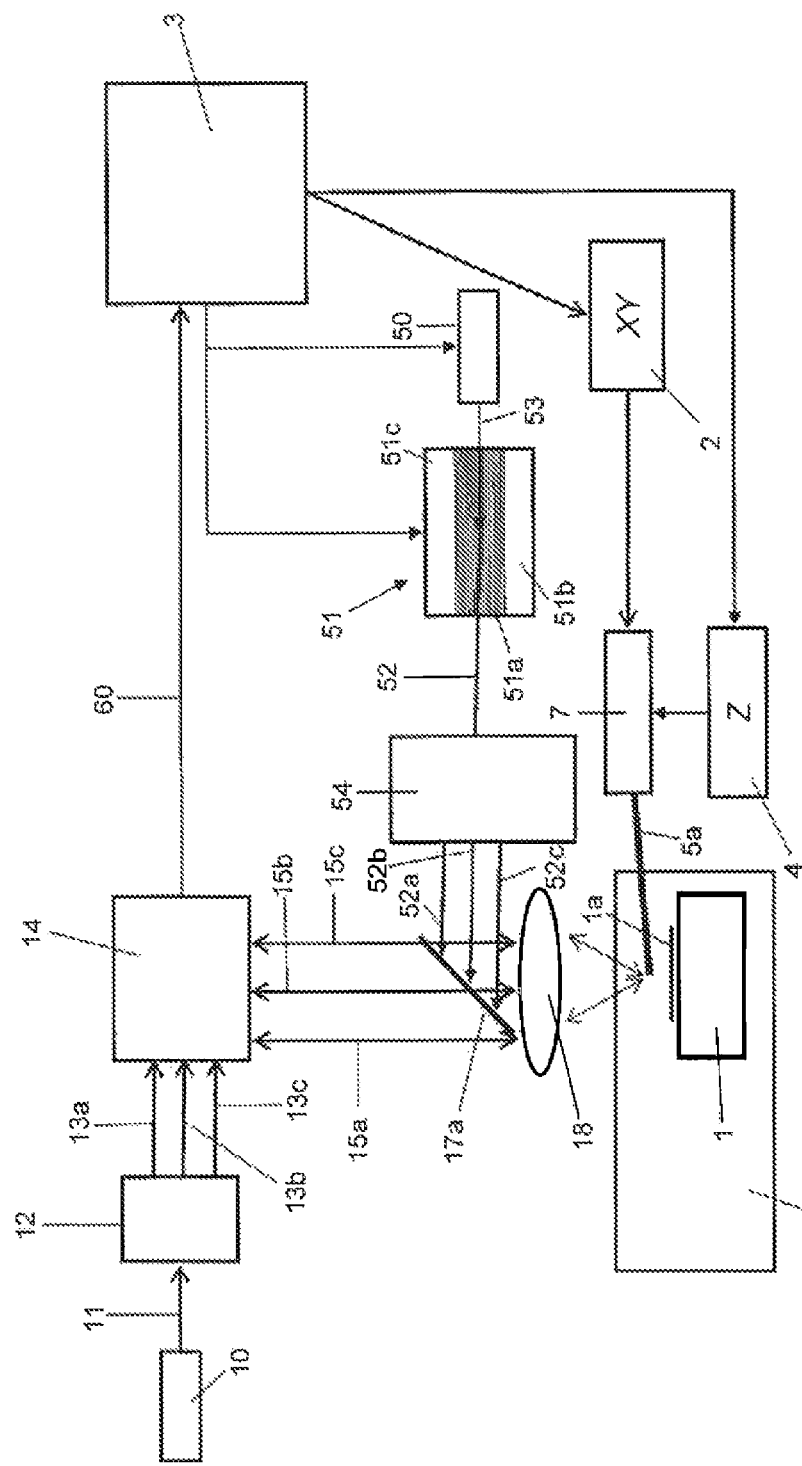
FIG. 9 is a schematic drawing of a biosensor.

A microcantilever biosensor will now be described with reference to FIG. 9. Many of the components are equivalent to those shown in FIG. 1, and the same reference numbers will be used for such equivalent components. However there is no requirement for probe array scanning, and the probe array is housed within a microfluidic cartridge 70 with an optical port that is capable of delivering the fluid to be analysed to the probe array while allowing optical access. It will be appreciated that such microfluidic systems are well known in the art and so will not be described further here. Tracking mirror 17 from FIG. 1 is omitted and replaced by an angled dichroic mirror 17a.

The probe array could be comprised of silicon or silicon nitride cantilevers as described above, except that no tip is necessary, as the active biosensor area of the cantilever is generally a well-defined area on the cantilever back, rather than on the tip. An area on the back of the cantilever will therefore be coated with a bimetallic layer for photothermal actuation, while another segment will typically be coated with gold for the biosensor, generally well away from both the actuation and detection lasers to avoid photodegradation. Gold is often used because it is suitable for the immobilization of thiol modified biochemical entities. These are the receptors which bind the target molecules (ligands) to the biosensor surface, thereby inducing surface stress and increasing the mass of the probe overall. It will be appreciated that many receptor-ligand combinations exist and are well known in the art, and so will not be described in detail here. The exact number of probes in the array also varies depending on the biosensor application, because clinical applications often have multiple target molecules. Typically arrays might consist of 10's or 100's of cantilevers, including both active and reference cantilevers. Reference cantilevers are typically used for temperature compensation during microfluidic operation and analyte measurement.

The cantilever probe array and microfluidic system 70 is incorporated into the parallel interferometer and photothermal scanning actuation system in much the same way as the SPM of FIG. 1. The biosensor array can be operated in either static or dynamic modes as described above. The dynamic mode will be described below in more detail.

In the dynamic mode the increase of mass of each probe produces a reduction in the resonant frequency that can be used to record the presence and concentration of the ligand in the microfluidic cavity surrounding the array. The parallel biosensor system is configured with the probe array suitably functionalized and aligned within the interferometer 14, with the cantilevers illuminated by the SLMs 12,54 to detect and actuate motion of the probes. In this case each probe is designed and fabricated to have the same resonant frequency, although some small variation is inevitable and not critical to the system operation. The analyte fluid is introduced into the microfluidic system 70 and is typically pumped to the probe array cavity for analysis, or driven by capillary action.

There are a number of detection schemes that can be used to sense the resonant frequency shift that takes place as the ligands bind to the receptors. In the case of amplitude detection, the probes are initially driven by the IR laser 50 at a frequency close to the unbound resonant frequency of the probe array. In the case considered here the drive frequency is below resonance, situated in a region of the resonant curve where the amplitude of probe oscillation varies approximately linearly with frequency. For any given probe, the new probe resonant frequency begins to drop as the ligand is bound, bringing the probe resonant frequency closer to the photothermal drive frequency. As a consequence the amplitude of the probe oscillation increases, approximately linearly with the bound mass of the ligands. Alternative detection schemes based on phase sensitive operation are known in the art and so will not be described here.

Both amplitude and phase detection schemes are less effective when the probes are heavily damped, as occurs when the probes are immersed in certain liquids, although they have the advantage of simplicity of operation as the same actuation drive signal can be used for all probes. However, sequential scanning allows individual control of each probe, thereby allowing improved detection schemes to be implemented. For example, in frequency modulation, the probe motion is fed back via a bandpass filter and phase shifter to drive the actuation signal, thereby creating a self-exciting oscillator running at the resonant frequency of the probe. This scheme has greater robustness when operating in liquid environments. The band-pass filter is used to eliminate spurious resonances that can occur. In order to implement the FM scheme with multiple probes, the actuation beam is scanned sequentially by the AOM over each probe. The actuation beam completes the self-excited feedback loop for each probe, ensuring the loop operates at the resonant frequency of the probe, which changes as the ligands bind to the surface. The output of each loop therefore corresponds to the shift in mass of the probe as a function of time. Other detection schemes, such as those based on quality factor enhancement, are known in the art (for example see U.S. Pat. No. 6,906,450) and could also be implanted with sequential scanning.

It will be appreciated that the simplified description given above could be amplified to take into account many of the more detailed considerations, such as compensation schemes and calibration, that are necessary for successful biosensor operation. Such details fall outside the scope of this application and are well known in the art.

The detection and actuation scheme described above offer many advantages for biosensor operation. Clinical applications often require multiple targets and hence probes, making conventional PSD detection impractical. The inventive system could in principle be scaled to several 100's of probes, this covering many clinical diagnostic requirements. The detection and actuation system is also flexible, and can be reconfigured by re-programming the controller 3 to operate with biosensor arrays of different dimensions and characteristics. The probe array itself is simple, cheap and disposable which is essential for many applications. The probe array, typically integrated into a microfluidic cartridge 70, can be introduced into the system quickly and the alignment completely automated as the actuation beam and sensing beamlets can be directed under computer control until the required optimum detection and photothermal actuation conditions are reached.

Figure 10:
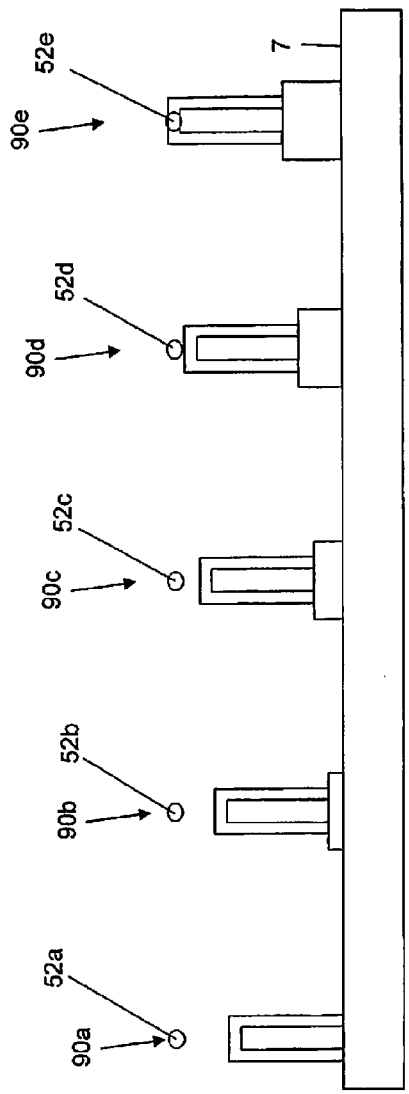
FIG. 10 shows an array of five probes and the illumination spots created by their associated actuation beamlets at a first time in a scan sequence.
Figure 11:
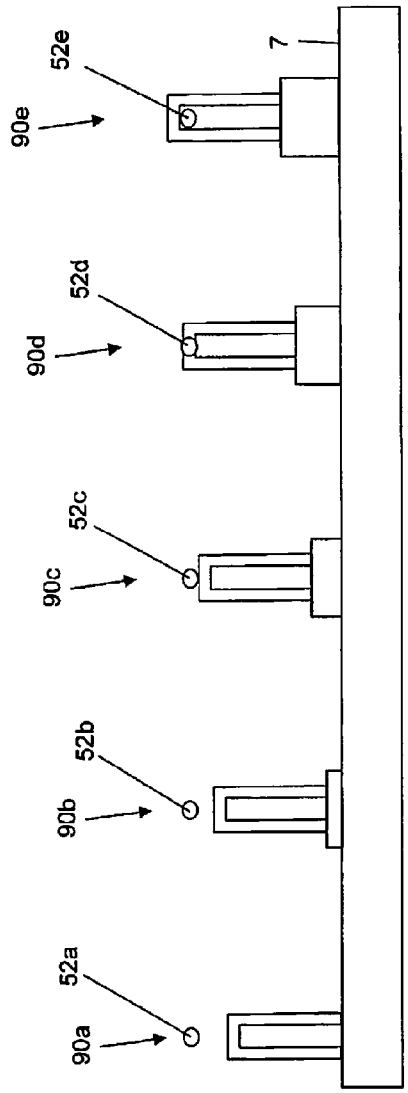
FIG. 11 shows the array of five probes and the illumination spots created by their associated actuation beamlets at a second time in a scan sequence.

In the example of FIGS. 5a and 5b the actuation beamlets are scanned across the probes perpendicular to the lengths of the cantilevers. FIG. 10 is a schematic view of an alternative array of five cantilever probes 90a-e viewed from above in which the actuation beamlets are instead scanned parallel to the lengths of the cantilevers. Each cantilever has a pair of cantilever arms separated by a gap, and a cross-bar joining the distal ends of the cantilever arms. The actuation beamlets 52a-e generate spots arranged in a straight line. The cross-bars are offset relative to the line of the actuation beamlets so that as the actuation beamlets are scanned down, only a single actuation beam illuminates a probe at any one time. FIG. 10 shows a first instant in the scan sequence in which only the probe 90e is illuminated. As the beamlets 52a-c move down together, beamlet 52e moves off the probe 90e and beamlet 52d moves onto the probe 90d as shown in FIG. 11, and so on. Thus as the actuation beamlets 52a-e scan across the probes, the probes are illuminated sequentially providing an effect analogous to a moiré pattern. In this illumination sequence the probes are illuminated one-by-one between adjacent probes from right to left—that is, in the sequence 5e,5d,5c, 5b,5a. However other illumination sequences are possible—for instance the probes may be illuminated two-by-two, or in a sequence which does not progress regularly between adjacent probes (for instance the sequence may be random or irregular such as 5a,5e,5b,5d,5c).

Although the invention has been described above with reference to one or more preferred embodiments, it will be appreciated that various changes or modifications may be made without departing from the scope of the invention as defined in the appended claims.

The invention claimed is:

1. A method of actuating a plurality of probes by delivering photothermal energy to the probes so that the probes are heated and deform relative to a sample, wherein the photothermal energy is delivered to the probes by:
   a. directing an input beam into an optical device;
   b. transforming the input beam with the optical device into a plurality of actuation beamlets which are not parallel with each other;
   c. scanning the actuation beamlets across the probes, wherein only a subset of the actuation beamlets illuminates a probe at any instant as the actuation beamlets scan across the probes and the probes are illuminated in an illumination sequence; and
   d. controlling the actuation beamlets so that different amounts of photothermal energy are delivered to at least two of the probes during the illumination sequence.

2. The method of claim 1 wherein the actuation beamlets are controlled so that different amounts of photothermal energy are delivered to at least two of the probes during the illumination sequence by modulating the input beam during the illumination sequence.

3. The method of claim 2 wherein the actuation beamlets are controlled so that different amounts of photothermal energy are delivered to at least two of the probes during the illumination sequence by modulating a power and/or angle of the input beam during the illumination sequence.

4. The method of claim 1 wherein the actuation beamlets are repeatedly scanned across the probes so the probes are illuminated in a series of illumination sequences, and the actuation beamlets are controlled so that different amounts of photothermal energy are delivered to at least two of the probes during one or more of the illumination sequences.

5. The method of claim 4 wherein each probe has a thermal time constant which is longer than each of the illumination sequences.

6. The method of claim 1 wherein only one of the actuation beamlets illuminates a probe at any instant.

7. The method of claim 1 wherein the actuation beamlets are scanned across the plurality of probes by changing an angle of the input beam into the optical device.

8. The method of claim 7 wherein the angle of the input beam is changed by an acousto-optic or electro-optic modulator.

9. The method of claim 1 wherein the plurality of probes comprises ten or more probes.

10. The method of claim 1 wherein the actuation beamlets are scanned across the probes via an objective lens.

11. The method of claim 1 wherein a spacing between at least two adjacent ones of the actuation beamlets is different to a spacing between at least two adjacent ones of the probes.

12. Actuation apparatus for actuating a plurality of probes by delivering photothermal energy to the probes so that the probes are heated and deform relative to a sample, the apparatus comprising:
   a. a radiation source for generating an input beam;
   b. an optical device arranged to transform the input beam into a plurality of actuation beamlets which are not parallel with each other;
   c. a scanner arranged to scan the actuation beamlets across the probes, wherein only a subset of the actuation beamlets illuminates a probe at any instant as the actuation beamlets scan across the probes and the probes are illuminated in an illumination sequence; and
   d. a controller arranged to control the actuation beamlets so that different amounts of photothermal energy are delivered to at least two of the probes during the illumination sequence.

13. The apparatus of claim 12 wherein the controller is arranged to control the actuation beamlets by modulating the input beam during the illumination sequence.

14. The apparatus of claim 12 wherein the scanner is arranged to change an angle of the input beam into the optical device.

15. The apparatus of claim 14 wherein the scanner comprises an acousto-optic or electro-optic modulator.

16. The apparatus of claim 12 further comprising an objective lens, wherein the scanner is arranged to scan the actuation beamlets across the probes via the objective lens.

17. The apparatus of claim 12 wherein a spacing between at least one adjacent pair of the actuation beamlets is different to a spacing between at least one adjacent pair of the probes.

18. A probe system comprising a plurality of probes; and actuation apparatus according to claim 12.

19. The probe system of claim 18 comprising ten or more probes.

* * * * *